United States Patent [19]

Eigen et al.

[11] Patent Number: 4,518,517

[45] Date of Patent: May 21, 1985

[54] NON-ANTIMICROBIAL DEODORANT CLEANSING COMPOSITION

[75] Inventors: Edward Eigen, East Brunswick; David Z. Twersky; Dina I. Brachman, both of Highland Park, all of N.J.

[73] Assignee: Colgate-Palmolive Company, New York, N.Y.

[21] Appl. No.: 475,817

[22] Filed: Mar. 16, 1983

[51] Int. Cl.$^3$ ............................ C11D 3/48; C11D 9/50
[52] U.S. Cl. ...................................... 252/107; 252/106; 252/108; 252/132; 252/546; 252/550; 252/555; 252/DIG. 16
[58] Field of Search ............... 252/106, 107, 108, 132, 252/174.17, 550, 555, 546, DIG. 16; 424/180, 361

[56] References Cited

U.S. PATENT DOCUMENTS

| | | | |
|---|---|---|---|
| 3,630,925 | 12/1971 | Buck | 252/107 |
| 3,975,313 | 8/1976 | Shelmire | 252/542 |
| 4,048,123 | 9/1977 | Hramchenko et al. | 252/545 |
| 4,061,585 | 12/1977 | Finn et al. | 252/174.17 |
| 4,077,890 | 3/1978 | Barker | 252/8.8 |
| 4,151,105 | 4/1979 | O'Roark | 252/145 |

FOREIGN PATENT DOCUMENTS 23772  11/1963  Japan.

OTHER PUBLICATIONS

CA 86:183821m (Watanabe).

*Primary Examiner*—Prince E. Willis
*Attorney, Agent, or Firm*—Herbert S. Sylvester; Murray M. Grill; John A. Stemwedel

[57] ABSTRACT

A deodorant body cleansing composition in the form of a liquid or solid opaque bar, comprising a detergent and a specific carbohydrate capable of reducing the odor-causing bacterial population on the body (skin and/or hair), without the use of antimicrobials. The essential deodorant agent which is a group of carbohydrates specifically effective against the odor-causing bacteria on the skin and/or hair, are mannose, glucose, and oligomers thereof, i.e. dimers, trimers, and tetramers.

16 Claims, No Drawings

NON-ANTIMICROBIAL DEODORANT CLEANSING COMPOSITION

BACKGROUND AND PRIOR ART

The present invention relates to novel body cleansing compositions which reduce the number of odor-causing bacteria on the skin, comprising a detergent and an effective amount of specific sugars that interfere with the mechanism by which the odor generating bacteria adhere to the skin. This method of reducing the bacterial population is deemed much safer than the use of antimicrobials, many of which have been prohibited.

Sugar solutions have been widely used in the preparation of transparent soap bars, as fully discussed in the text *The Modern Soap and Detergent Industry* by Geoffrey Martin, Vol. II, Sec. I, 69–75 and Sec. IX, 25 (1951). All of said transparent soap bars contain fatty acid soap as the cleansing agent, and cane sugar (sucrose), alcohol and glycerine to impart transparency to the soap bar.

Transparent solid detergent products containing N-long chain acyl acidic aminoacid detergents and a clarifying agent which may be a carbohydrate such as glucose, fructose or sucrose in the weight ratio of 9:1 to 4:6 respectively, are disclosed in Japanese Patent JA 0025465 1 (February 1980). Japanese Patent JA 0076499 (June 1981) also discloses an acidic aminoacid salt and 1-30% by weight of a clarifying agent which may be glycerine, diglycerine, ethylene glycol, propylene glycol, sorbitol, glucose, sugar, urea, etc.

An aqueous transparent detergent composition comprising a sucrose fatty acid ester as the detergent, an organic acid such as malic or tartaric acid and 5-30% of a saccharide such as sucrose or sorbitol to improve detergency and the stable transparency of the composition, is disclosed in U.S. Pat. No. 3,872,020. A clear liquid shaving cream to provide a transparent film on the skin which permits a complete shave without rinsing of the razor or the skin, is disclosed in U.S. Pat. No. 3,072,535. This composition contains a lanolin derivative, sodium carboxymethylcellulose, a germicide and preferably a saccharide such as sucrose. This preferred component is added to the above composition to alter its surface and flow characteristics when sprayed from a pressurized container.

Dextrose sugar has been used in a disinfectant/cleanser composition as an eye irritancy mitigant in a composition containing a quaternary ammonium germicide as shown in U.S. Pat. No. 4,366,151.

A rinse agent concentrate for the machine washing of dishes, containing beet sugar, cane sugar or dextrin is disclosed in U.S. Pat. No. 3,592,774, in order to obtain spot-free dishes.

A deodorant and germicidal solid product for toilets and urinals is disclosed in U.S. Pat. No. 3,630,925, wherein sugar constitutes the slowly dissolving carrier for the soap and germicidal agent.

Sugars such as sucrose, glucose, dextrin and the like have also been used in silicate containing soaps to prevent efflorescence to produce a clearer smoother mix as shown in *Soluble Silicate*, Vol. 2, by James Vail, D. Sc. 16-20 (1952).

The purpose of the sugar component in the cleansing compositions of the above cited prior art is to provide transparent soaps and detergent bars, to improve detergency and transparency and flow characteristics of liquid compositions; as an irritancy mitigant in compositions containing germicides; as a carrier in a solid product to provide the proper dissolution of the soap and germicide contained therein; and as an efflorescence deterrant in silicate soaps.

However, none of said sugar-containing cleansing compositions provide a means of reducing the odor-causing bacterial population on the body and hair without the use of antimicrobials.

SUMMARY OF THE INVENTION

It has been unexpectedly found that the addition of about 1–15% by weight of a carbohydrate selected from the group consisting of glucose, mannose, oligomers thereof and mixtures thereof, to a body cleansing composition produces a deodorant composition which reduces the odor-causing microbial population on the skin, without the use of antimicrobials.

Accordingly, a primary object of present invention is to provide a body cleansing composition which reduces body odor, without the use of antimicrobial agents.

Another object of the present invention is to provide a non-antimicrobial deodorant cleansing composition comprising an anionic detergent and a specified carbohydrate capable of reducing the odor-causing bacterial population on the skin.

Another object of present invention is to provide a deodorizing body cleansing composition in the form of a liquid or an opaque solid bar.

Another object of present invention is to provide a deodorizing skin cleansing composition containing an effective amount of glucose and/or mannose and/or oligomers thereof to inhibit odor-causing bacterial attachment to the skin.

Still another object of this invention is to provide a process for simultaneously cleansing and deodorizing the body by washing with the carbohydrate-containing detergent composition of this invention.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel deodorant body cleansing composition of this invention comprises at least one carbohydrate selected from the group consisting of glucose, mannose and oligomers thereof as the essential deodorant agent, in an amount effective to reduce the odor-causing bacterial population on the body without the use of antimicrobials, in a detergent-containing vehicle. Several of these antimicrobials have been banned in the past (hexachlorophene, tribromsalicylanilide) as unsafe and others in use now are still being reviewed by the FDA. The vehicle may be in the form of a liquid or opaque solid bar.

More specifically, present invention relates to a deodorant detergent composition containing as the essential deodorant about 1–15% and preferably 2.5–10% by weight of at least one carbohydrate having specificity to the lectins of the odor-causing bacterial organisms, whereby said carbohydrate reduces body odors by detachment of said odor-causing organisms from the skin;

and to a process of simultaneously cleansing and deodorizing the human body by washing with said carbohydrate-containing detergent composition.

The sugar specificity of lectins on organisms such as Escherichia coli was reported in *Nature*, Vol. 265, No. 5595, pp. 623–625, Feb. 17, 1977, wherein it was found that mannose acts as a receptor for binding *E. coli*, but not streptococcus. These findings allegedly may provide an explanation of the mechanism of bacterial adherence on mucosal tissues. The adherence of *E. coli* to human epithelial cells by binding specifically and reversibly to mannose residues on the surface of the epithelial cells is also disclosed in *Trends in Biochemical Sciences*, July 1978, pp. 159–160. It was found therein that at low concentrations, only D-mannose, methyl α-D-mannoside and yeast mannan, a polymer of D-mannose, inhibited the bacterial attachment of the *E. coli* to epithelial cells. Other sugars had no effect. The *E. coli* possess a lectin on its surface which specifically binds to the mannose, and is responsible for attachment on epithelial cells, said mannose-specific lectin functioning as a binding mediator.

It has now been found that said lectin technology can be used as a means of reducing the numbers of odor-causing bacteria on the skin. Lectins are proteins or glyco-proteins which have an affinity for specific sugars. These materials are present in the cell membranes of bacteria and is one mechanism by which they adhere to surfaces. The lectin-sugar bond can be broken with an excess of the same sugar. This has been demonstrated with the detachment of *E. coli* from epithelial cells with mannose, as described above. Stratum corneum contains sugars which could be the hook on which bacteria attach. It has been shown by in vivo tests, that washing axillae with a mixture of glucose and mannose dissolved in either 0.2% sodium lauryl sulfate or a liquid soap formulation results in less odor formation than washing only with the detergents containing no additives. It has also been found that a significant decrease in the numbers of lipophilic diphtheroids is present in axillae that are washed with the sugar-containing liquid soap as compared with liquid soap with ano additives. Lipophilic diphtheroids are bacteria responsible for a major portion of underarm odor.

The sugar specificity of the bacteria in question, can be determined by immobilizing various sugars onto an inert matrix, mixing a known bacterial suspension with the sugar linked matrix, eluting the unattached bacteria and determining the amount of bacteria still attached to the matrix by turbidity measurements.

The inhibition of bacterial attachment to the skin in the presence of specific sugars has also been viewed microscopically, using the following procedure:

A 2.0 cm×0.5 cm piece of human stratum corneum was placed in 10 ml of physiological (0.9%) saline solution and blended in a Waring blender for 5 minutes. Big chunks of skin remained but the saline solution was turbid. This suspension was centrifuged for 30 minutes at 3000 RPM in a table top centrifuge. The supernatant liquid was poured off and saline was added to a final volume of 3 ml. A bacterial suspension was made by suspending one swab of small colony diptheroids into 3 ml of sterile saline. This was then aliquotted into 4 0.5 ml samples. To Sample 1, S1, nothing was added. To S2, 2.5% galactose; to S3, 2.5% mannose; to S4, 2.5% N-acetyl glucosamine. To each of these, 0.5 ml of the skin suspension was added, vigorously mixed and incubated 30 minutes at 37° C.

Following incubation, the samples were made into dry mounts, fixed and stained with crystal violet for one minute. They were then looked at under the microscope.

Results:

S1. Large numbers of bacteria appeared to be attached to the skin cells.

S2. Again large numbers of bacteria appeared to be attached to the skin cells.

S3. Noticeably fewer numbers of bacteria appeared to be attached to the skin.

S4. Large numbers of bacteria appeared to be attached to the skin.

These results show the specificity of mannose to the diptheroid bacteria which is responsible for a major portion of underarm odor, as well as its ability to inhibit bacterial attachment to the skin, thereby reducing bacterial population thereon and, hence, odor. Neither the galactose nor the N-acetyl glucosamine had an effect on the diptheroid bacterial population on the skin.

Using the procedure above, the following seven samples were prepared and viewed microscopically to determine if bacterial attachment to skin can be inhibited by other sugars:

S1. 0.5 ml skin suspension+0.5 ml bacterial suspension

S2. 0.5 ml skin suspension+0.5 ml sterile saline

S3. 0.5 ml skin suspension+0.5 ml bacterial suspension and 30 mg mannose

S4. 0.5 ml skin suspension+0.5 ml bacterial suspension and 30 mg N-acetyl glucosamine S5. 0.5 ml skin suspension+0.5 ml bacterial suspension and 30 mg galactose S6. 0.5 ml skin suspension+0.5 ml bacterial suspension and 30 mg ribose S7. 0.5 ml skin suspension+0.5 ml bacterial suspension and 30 mg N-acetyl galactosamine These were vigorously mixed and incubated at 37° C. for 30 minutes. Dry mounts were then prepared, fixed, stained with crystal violet for one minute and read under the microscope.

Results:

S1. Bacterial attachment seen

S2. No bacterial attachment seen

S3. Lower bacterial attachment seen

S4. Bacterial attachment seen

S5. Bacterial attachment seen

S6. Bacterial attachment seen

S7. Bacterial attachment seen

Mannose is the only sugar that shows inhibition of bacterial attachment, as shown by fewer bacteria attached to the skin sample.

Additional tests made with other sugars including fructose, lactose, maltose, sucrose, raffinose and rhamnose also showed a greater amount of bacteria attached to the skin than when treated with mannose. This proves the specificity of mannose to the diptheroid bacteria.

Blond hair incubated with an axillary culture was examined for bacterial attachment. Several strands of hair were removed, washed in deionized (DI) $H_2O$, stained and looked at under the microscope. There were many bacteria present on the hair, rods and cocci. Different sugars were tried to rinse the bacteria off the hair. 5% sugar solutions were prepared, the hair soaked in them for 30 minutes, washed in DI $H_2O$, stained and looked at microscopically. The hair was treated with DI $H_2O$, dextrose, mannose and a mixture of dextrose and mannose. No quantitative counts were done, but it appears qualitatively that the hair treated with dextrose and mannose had less bacteria.

Accordingly, it has been found that the specific sugars mannose, glucose and oligomers thereof in a detergent vehicle are effective for both deodorizing and cleansing the body by simply washing therewith. In vivo odor evaluation tests using 0.2% aqueous sodium lauryl sulfate vehicle containing 5% dextrose and 5% mannose as the washing medium (5 ml test solution pipetted into a washcloth and used for 30 seconds, followed by rinsing thoroughly with water) on armpits with moderate to heavy odor resulted in greater deodorization of the armpits and for a longer time period than when using said detergent vehicle per se.

The deodorant mechanism of the specific carbohydrate, mannose and/or glucose (dextrose) in this invention, is totally different from conventional deodorants which rely on the neutralization of odors through acid/base chemical interaction. Likewise, it does not function as the prior art antibacterial agents which inhibit the growth of bacteria. These sugars function as a deodorant by reducing the odor-causing bacterial population on the skin by the selective removal of aerobic diphtheroid bacteria which are responsible for the bulk of axillary odor. More specifically, the specific sugars interfere with the mechanism by which said odor generating bacteria adhere to the skin so that the detached bacteria can simply be washed from the skin.

The specific sugars, mannose, glucose and oligomers thereof are effective deodorant agents in aqueous liquid detergent vehicles and in solid opaque detergent bars, and will usually constitute about 1-15% and preferably 2.5-10% by weight of the total composition.

An essential ingredient of present deodorant detergent compositions is an anionic surface active agent containing a sulfonate, sulfate, carboxylate or phosphate as the anionic water solubilizing group. Examples of suitable anionic detergents include the soaps, such as the water-soluble salts of higher fatty acids or rosin acids, such as may be derived from fats, oils and waxes of animal, vegetable or marine origin, e.g., the sodium soaps of tallow, grease, coconut oil, tall oil and mixtures thereof; and the sulfated and sulfonated synthetic detergents, particularly those having about 8 to 26, and preferably about 12 to 22, carbon atoms to the molecule. Examples of suitable synthetic anionic detergents include the higher olefin sulfonates such as sodium $C_{14-16}$ alpha olefin sulfonate; the higher alkyl mononuclear aromatic sulfonates such as the higher alkyl benzene sulfonates containing from 10-16 carbon atoms in the alkyl group in a straight or branched chain, e.g., the sodium salts of decyl, undecyl, dodecyl (lauryl), tridecyl, tetradecyl, pentadecyl, or hexadecyl benzene sulfonate and the higher alkyl toluene, xylene and phenol sulfonates; alkyl naphthalene sulfonate, ammonium diamyl naphthalene sulfonate, and sodium dinonyl naphthalene sulfonate; sulfated aliphatic alcohols such as sodium lauryl and hexadecyl sulfates, triethanolamine lauryl sulfate, and sodium oleyl sulfate; sulfated alcohol ethers, such as lauryl, tridecyl, or tetradecyl sulfates including 2-4 ethylene oxide moieties; sulfated and sulfonated fatty oils, acids or esters, such as the sodium salts of sulfonated castor oil and sulfated red oil; sulfated hydroxyamides such as sulfated hydroxy-ethyl lauramide; sodium salt of lauryl sulfoacetate; sodium salt of dioctyl sulfosuccinate, and the sodium salt of oleyl methyl tauride.

Also included within the ambit of the invention are the sulfuric acid esters of polyhydric alcohols incompletely esterified with higher fatty acids, e.g., coconut oil monoglyceride monosulfate, tallow diglyceride monosulfate; and the hydroxy sulfonated higher fatty acid esters such as the higher fatty acid esters of low molecular weight alkylol sulfonic acids, e.g., oleic acid ester of isethionic acid.

The anionic surfactants most often used are the ammonium, mono-, di- and triethanolamine, and alkali metal (sodium and potassium) salts of the higher alkyl benzene sulfonates, higher olefin sulfonates, the higher alkyl sulfates, the higher fatty acid monoglyceride sulfates and the sulfated ethoxylated alcohols and mixtures thereof. The anionic surface active agent typically comprises about 0.2-35% and preferably 5-25% by weight of the liquid formulation; and comprises about 65-96% and preferably 70-90% by weight of the opaque solid bar.

Although an anionic surface active agent is preferred, a nonionic surface active agent may replace a portion of the anionic surface active agent, and constitute about 0-10% by weight of the composition. The nonionic surfactants useful herein are well-known in the art, and include the condensation of an alkyl phenol, an alkyl amine, an aliphatic alcohol, or a fatty acid with sufficient ethylene oxide to produce a compound having a polyethylene chain within the molecule, i.e., a chain composed of recurring ($-O-CH_2-CH_2-$) groups. Examples of this type of surfactant are compounds produced by condensing about 5-30, preferably about 8-16, moles of ethylene oxide with one mole of an alkyl phenol having about 0-15, preferably 7-10, carbon atoms in the alkyl group; an alkyl amine having about 10-20, preferably 12-16, carbon atoms in the alkyl group; an aliphatic alcohol having about 9-20, preferably 12-16, carbon atoms in its molecule; and a fatty acid having about 10-20, preferably 12-16, carbon atoms in its molecule.

An optionally preferred ingredient in present formulation is ethylene diamine tetraacetic acid tetrasodium salt (EDTA) in minor amounts of about 0.5-2% by weight, which assists in the detachment of the bacteria from the skin, by chelating any cation such as calcium, magnesium, and the like which may be found in the environment.

The detergent compositions of this invention may also contain conventional additional components such as coloring agents and perfumes; hydrotropic materials such as ammonium or sodium toluene or xylene sulfonate, salt, ethyl alcohol; preservatives such as formaldehyde, hydrogen peroxide, methyl, ethyl or propyl p-hydroxy benzoate, hydantoin; foam enhancing agents such as the amine oxides e.g., dimethyldodecyl amine oxide, bis(2-hydroxyethyl)dodecyl amine oxide and N-dodecyl morpholine oxide, and the mono- and the di-alkylolamides of $C_{10}$-$C_{14}$ carboxylic acids such as the diethanolamide of coconut fatty acids, lauric or coco monoethanolamide, myristic mono-3-propanolamide, capric diethanolamide, lauric myristic mono- and diethanolamide; emolients and other ingredients to enhance the feel of the product such as lanolin, glycerine, the polymeric quaternary ammonium salts and the betaines. These optional additives preferably do not exceed 5% by weight of the composition.

The present liquid and opaque deodorant detergent bar compositions used for body cleansing and deodorizing are readily made by conventional mixing methods.

DETAILED DESCRIPTION OF THE INVENTION

The following examples are merely illustrative of the invention, but it is understood that the invention is not limited thereto. All amounts of various ingredients are by weight unless otherwise specified.

EXAMPLES 1-3

| Liquid Deodorant Detergents | | | |
|---|---|---|---|
| Ingredient | Ex. 1 % | Ex. 2 % | Ex. 3 % |
| Deionized Water | Q.S. | Q.S. | Q.S. |
| Sodium Chloride | .80 | .80 | .80 |
| EDTA Tetrasodium[1] | .062 | 1.00 | .062 |
| Coco Monoethanolamide | 5.10 | 5.10 | 5.10 |
| Cocamidopropyl Betaine | .90 | .90 | .90 |
| PEG-75 Lanolin[2] | 1.00 | 1.00 | 1.00 |
| Glycerine | 1.50 | 1.50 | 1.50 |
| Quaternium-41[3] | 1.00 | 1.00 | 1.00 |
| Sodium $C_{14-16}$ Alpha Olefin Sulfonate | 21.00 | 21.00 | 21.00 |
| DMDM Hydantoin[4] | .10 | .10 | .10 |
| Citric Acid (50%) | Q.S.* | Q.S.* | Q.S.* |
| Mannose | — | 5.00 | — |
| Glucose | — | 5.00 | — |
| Trichloro Hydroxy Diphenyl Ether | — | — | .25 |

*For adjustment to pH 7.30
[1]Ethylenediamine tetraacetic acid tetrasodium
[2]Polyethylene glycol condensed with lanolin
[3]Polymeric quaternary ammonium salt
[4]1,3-dimethylol-5,5-dimethyl hydantoin The axillae of ten (10) male volunteers were washed twice daily (Monday through Thursday) with 5 ml of the samples of the above examples. After a one minute washing, the axilla was thoroughly rinsed with tap water.

Odor evaluations were made before each washing Monday through Wednesday and again on Thursday before each washing with an additional evaluation at noon time. On Friday, there was an a.m. odor evaluation with no treatment. Odor evaluations were graded on a 0 to 8 scale, 0 being no noticeable odor and 8 being a strong repugnant odor. Grades represented a combined score for the two major odoriferous compounds, isovaleric acid and androstenone.

Quantitative bacteriological cultures were obtained by the detergent scrub method of Williamson, P. and Kligman, A. M.: A New Method for the Quantitative Investigation of Cutaneous Bacteria. J. Invest. Derm. 45 #6, 498–503, 1965.

The results of the test showed that both the test soaps and the vehicle were more efficient in reducing the number of aerobic diphtheroids than aerobic cocci; and the test soap of Example 2 produced a greater reduction in the aerobic diphtheroid count than the vehicle of Example 1 and the antimicrobial-containing soap of Example 3. Both test soaps and the vehicle per se produced a meaningful reduction in axillary odor and axillary aerobic diphtheroids, but the test soap of Example 2 (sugar-containing) was superior both in the magnitude and the duration of these effects.

These superior deodorant results exhibited by Example 2 are unexpected in view of the fact that addition of the active ingredient which is not an antibacterial agent but specific sugars, appears to be working by preferentially affecting the adherence of aerobic diphtheroids. Aerobic diphtheroids produce the pungent malodorant, androstenone, as well as isovaleric acid, while aerobic cocci produce only isovaleric acid. Reduction of diphtheroids results in a more profound odor reduction than a reduction of cocci alone.

EXAMPLE 4

| Aqueous Deodorant Detergent Solution | |
|---|---|
| Ingredients | % |
| Sodium lauryl sulfate | 0.2 |
| Dextrose | 5.0 |
| Mannose | 5.0 |
| Deionized Water | Q.S. |

The sodium lauryl sulfate, mannose and dextrose is dissolved in water.

This composition exhibits deodorant properties in addition to cleansing properties.

EXAMPLE 5

| Opaque Soap Bar | |
|---|---|
| Ingredient | % |
| Soap chips 75% tallowate 25% coconut oil fatty acids | 87.8 |
| Stannic chloride | 0.2 |
| Citric acid (50%) | Q.S.* |
| Mannose | 5.0 |
| Glucose | 5.0 |
| EDTA | 1.0 |

*For adjustment to pH 10–10.5

The soap chips are milled one time in a soap miller to give small flakes which are then mixed with all the other ingredients in an amalgamator (Hobart Mixer), or mixed by hand. This mixture is milled again to achieve uniform distribution of the ingredients. This soap mixture is put in a plodder and extruded into long strips of soap. The strips are cut into bar sized pieces and pressed into soap bars.

EXAMPLE 6

| Opaque Detergent Bar | |
|---|---|
| Ingredient | % |
| Detergent chips 94.515% sulfated hydrogenated coco-fatty acid monoglycerides 5.485% $C_{16-20}$ alcohol or $C_{18-20}$ alcohol | 78.5 |
| NaCl | 10.0 |
| Perfume | 0.5 |
| EDTA | 1.0 |
| Mannose | 5.0 |
| Glucose | 5.0 |

This detergent bar is prepared as in Example 5.

Variations in the above formulations may be made. For example other anionic surface active agents may be substituted for the specific anionics in the examples. Also, small amounts of a nonionic surface active agent may replace a portion of the anionic surface active agent and still achieve the deodorant properties attributable to the specific group of carbohydrates defined herein.

Likewise, the mannose per se or the glucose per se, or a mannose-dimer, trimer, or tetramer, or a glucose-dimer, trimer, or tetramer may be substituted for the mixture of mannose and glucose in the examples with the same deodorant results.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A deodorant body cleansing composition comprising at least one carbohydrate selected from the group consisting of glucose, mannose and oligomers thereof as the essential deodorant agent in an amount of about 2.5–10%, effective to reduce the odor-causing bacterial population on the body, without the use of antimicrobials, in an anionic detergent-containing vehicle.

2. The composition of claim 1, wherein the detergent-containing vehicle is in the form of a liquid.

3. The composition of claim 1, wherein the detergent-containing vehicle is in the form of an opaque solid bar.

4. A deodorant body cleansing composition comprising a 1-1 mixture of mannose and glucose as the essential deodorant agent in an amount effective to reduce the odor-causing bacterial population of the body, without the use of antimicrobials, in a detergent-containing vehicle.

5. The composition of claim 4, wherein the detergent in the vehicle is an anionic surfactant.

6. The composition of claim 4, wherein the detergent in the vehicle is a mixture of anionic and nonionic surface active agents.

7. The composition of claim 5, wherein the detergent-containing vehicle is in the form of a liquid.

8. The composition of claim 5, wherein the detergent-containing vehicle is an opaque solid bar.

9. The composition of claim 7, wherein the anionic surface active agent constitutes about 5–35% by weight of the composition.

10. The composition of claim 8, wherein the anionic surface active agent constitutes about 65–96% by weight of the composition.

11. The composition of claim 7, wherein the anionic surfactant is sodium $C_{14-16}$ alpha olefin sulfonate.

12. The composition of claim 7, wherein the anionic surfactant is sodium lauryl sulfate.

13. The composition of claim 8, wherein the anionic surface active agent is sulfated hydrogenated coco-fatty acid monoglycerides.

14. The composition of claim 8, wherein the anionic surface active agent is a mixture of tallowate soap and coconut oil fatty acid soaps.

15. The composition of claim 4 or 1, which also contains a minor amount of the tetrasodium salt of ethylenediamine tetraacetic acid.

16. A method of simultaneously cleansing and deodorizing the body comprising washing with the composition of claim 4 or 1.

* * * * *